United States Patent
Glossop

(10) Patent No.: US 9,661,991 B2
(45) Date of Patent: May 30, 2017

(54) SYSTEM, METHOD AND DEVICES FOR NAVIGATED FLEXIBLE ENDOSCOPY

(75) Inventor: Neil David Glossop, Toronto (CA)

(73) Assignee: Koninklijke Philips N.V., Eindhoven (NL)

(*) Notice: Subject to any disclaimer, the term of this patent is extended or adjusted under 35 U.S.C. 154(b) by 2312 days.

(21) Appl. No.: 11/508,835

(22) Filed: Aug. 24, 2006

(65) Prior Publication Data
US 2007/0055128 A1 Mar. 8, 2007

Related U.S. Application Data

(60) Provisional application No. 60/710,657, filed on Aug. 24, 2005.

(51) Int. Cl.
*A61B 5/05* (2006.01)
*A61B 1/005* (2006.01)
(Continued)

(52) U.S. Cl.
CPC .............. *A61B 1/005* (2013.01); *A61B 1/31* (2013.01); *A61B 5/06* (2013.01); *A61B 5/065* (2013.01);
(Continued)

(58) Field of Classification Search
CPC ................ A61B 19/5244; A61B 19/50; A61B 2019/5255; A61B 8/0841
(Continued)

(56) References Cited

U.S. PATENT DOCUMENTS

| 3,021,842 A | 2/1962 | Flood |
| 4,080,706 A | 3/1978 | Heilman et al. ................ 29/173 |

(Continued)

FOREIGN PATENT DOCUMENTS

| AU | 6367896 | 2/1997 |
| AU | 722539 | 8/2000 |

(Continued)

OTHER PUBLICATIONS

"Automatic Centerline Extraction for Virtual Colonoscopy" by M. Wan et al. IEEE Trans Med Imag. vol. 21, No. 12, pp. 1450-1460, 2002.*
(Continued)

*Primary Examiner* — Tse Chen
*Assistant Examiner* — Jason Ip

(57) ABSTRACT

The invention provides a method and system for performing an image-guided endoscopic medical procedure. The invention may include registering image-space coordinates of a path of a medical instrument within the anatomy of a patient to patient-space coordinates of the path of the medical instrument within the anatomy of the patient. In some embodiments, the image space coordinates of the path of the medical instrument may be predicted coordinates such as, for example, a calculated centerline through a conduit-like organ, or a calculated "most likely path" of the medical instrument within the anatomy of the patient. In other embodiments, the path of the medical instrument may be an actual path determined using intra-operative images of the patient's anatomy with the medical instrument inserted therein. The registered instrument may then be navigated to one or more items of interest for performance of the endoscopic medical procedure.

21 Claims, 9 Drawing Sheets

(51) Int. Cl.
- *A61B 1/31* (2006.01)
- *A61B 5/06* (2006.01)
- *G06T 19/00* (2011.01)
- *A61B 90/00* (2016.01)
- *A61B 34/20* (2016.01)
- *A61B 6/12* (2006.01)
- *A61B 34/10* (2016.01)

(52) U.S. Cl.
CPC ............ *A61B 34/20* (2016.02); *A61B 90/36* (2016.02); *G06T 19/003* (2013.01); *A61B 6/12* (2013.01); *A61B 34/10* (2016.02); *A61B 90/361* (2016.02); *A61B 2034/107* (2016.02); *A61B 2034/2051* (2016.02); *A61B 2090/397* (2016.02); *G06T 2210/41* (2013.01)

(58) Field of Classification Search
USPC .............. 600/424, 407, 427; 606/1; 128/899
See application file for complete search history.

(56) References Cited

U.S. PATENT DOCUMENTS

| | | | | |
|---|---|---|---|---|
| 4,279,252 | A | 7/1981 | Martin | 128/349 R |
| 4,697,595 | A | 10/1987 | Breyer et al. | 128/660 |
| 4,722,056 | A | 1/1988 | Roberts et al. | 364/413 |
| 4,777,951 | A | 10/1988 | Cribier et al. | 128/344 |
| 4,887,606 | A | 12/1989 | Yock et al. | 128/662.05 |
| 4,895,168 | A | 1/1990 | Machek | 128/772 |
| 4,935,019 | A | 6/1990 | Papp, Jr. | 604/362 |
| 4,961,433 | A | 10/1990 | Christian | 128/772 |
| 5,042,486 | A | 8/1991 | Pfeiler et al. | 128/653 R |
| 5,045,080 | A | 9/1991 | Dyer et al. | 604/362 |
| 5,116,345 | A | 5/1992 | Jewell et al. | 606/130 |
| 5,187,658 | A | 2/1993 | Cline et al. | 364/413.13 |
| 5,204,625 | A | 4/1993 | Cline et al. | 324/306 |
| 5,207,675 | A | 5/1993 | Canady | 606/40 |
| 5,211,165 | A | 5/1993 | Dumoulin et al. | 128/653.1 |
| 5,221,283 | A | 6/1993 | Chang | 606/130 |
| 5,247,935 | A | 9/1993 | Cline et al. | 128/653.2 |
| 5,251,127 | A | 10/1993 | Raab | 364/413.13 |
| 5,251,635 | A | 10/1993 | Dumoulin et al. | 128/653.2 |
| 5,255,680 | A | 10/1993 | Darrow et al. | 128/653.1 |
| 5,265,610 | A | 11/1993 | Darrow et al. | 128/653.1 |
| 5,271,400 | A | 12/1993 | Dumoulin et al. | 128/653.2 |
| 5,275,165 | A | 1/1994 | Ettinger et al. | 128/653.2 |
| 5,290,266 | A | 3/1994 | Rohling et al. | 604/272 |
| 5,291,010 | A | 3/1994 | Tsuji | 250/208.1 |
| 5,291,890 | A | 3/1994 | Cline et al. | 128/653.2 |
| 5,304,933 | A | 4/1994 | Vavrek et al. | 324/318 |
| 5,305,203 | A | 4/1994 | Raab | 364/413.13 |
| 5,307,812 | A | 5/1994 | Hardy et al. | 128/653.2 |
| 5,318,025 | A | 6/1994 | Dumoulin et al. | 128/653.2 |
| 5,323,779 | A | 6/1994 | Hardy et al. | 128/653.2 |
| 5,327,884 | A | 7/1994 | Hardy et al. | 128/653.2 |
| 5,353,808 | A | 10/1994 | Viera | 128/772 |
| 5,365,927 | A | 11/1994 | Roemer et al. | 128/653.2 |
| 5,368,031 | A | 11/1994 | Cline et al. | 128/653.2 |
| 5,368,032 | A | 11/1994 | Cline et al. | 128/653.2 |
| 5,377,678 | A | 1/1995 | Dumoulin et al. | 128/653.1 |
| 5,383,454 | A | 1/1995 | Bucholz | 128/653.1 |
| 5,383,465 | A | 1/1995 | Lesny et al. | 128/662.05 |
| 5,386,828 | A | 2/1995 | Owens et al. | 128/653.1 |
| 5,389,101 | A | 2/1995 | Heilbrun et al. | 606/130 |
| 5,391,199 | A | 2/1995 | Ben-Haim | 607/122 |
| 5,396,905 | A | 3/1995 | Newman et al. | 128/849 |
| 5,400,383 | A | 3/1995 | Yassa et al. | 378/98.2 |
| 5,437,277 | A | 8/1995 | Dumoulin et al. | 128/653.1 |
| 5,443,066 | A | 8/1995 | Dumoulin et al. | 128/653.1 |
| 5,443,068 | A | 8/1995 | Cline et al. | 128/653.5 |
| 5,445,150 | A | 8/1995 | Dumoulin et al. | 128/653.1 |
| 5,465,732 | A | 11/1995 | Abele | 128/772 |
| 5,490,840 | A | 2/1996 | Uzgiris et al. | 604/22 |
| 5,493,598 | A | 2/1996 | Yassa et al. | 378/98.2 |
| 5,526,812 | A | 6/1996 | Dumoulin et al. | 128/653.1 |
| 5,526,814 | A | 6/1996 | Cline et al. | 128/653.2 |
| 5,558,091 | A | 9/1996 | Acker et al. | 128/653.1 |
| 5,603,318 | A | 2/1997 | Heilbrun et al. | 128/630 |
| 5,645,065 | A | 7/1997 | Shapiro et al. | 128/653.1 |
| 5,646,524 | A | 7/1997 | Gilboa | 324/207.17 |
| 5,646,525 | A | 7/1997 | Gilboa | 324/207.17 |
| 5,647,373 | A | 7/1997 | Paltieli | 128/749 |
| 5,705,014 | A | 1/1998 | Schenck et al. | 156/272.4 |
| 5,713,858 | A | 2/1998 | Heruth et al. | 604/93 |
| 5,715,166 | A | 2/1998 | Besl et al. | 364/474.24 |
| 5,715,822 | A | 2/1998 | Watkins et al. | 128/653.5 |
| 5,740,802 | A | 4/1998 | Nafis et al. | 128/653.1 |
| 5,749,835 | A | 5/1998 | Glantz | 600/424 |
| 5,769,790 | A | 6/1998 | Watkins et al. | 600/439 |
| 5,769,861 | A | 6/1998 | Vilsmeier | 606/130 |
| 5,800,352 | A * | 9/1998 | Ferre et al. | 600/407 |
| 5,848,969 | A | 12/1998 | Panescu et al. | 600/462 |
| 5,857,032 | A | 1/1999 | Wang et al. | 382/154 |
| 5,873,845 | A | 2/1999 | Cline et al. | 601/3 |
| 5,880,976 | A | 3/1999 | DiGioia III et al. | 364/578 |
| 5,931,786 | A | 8/1999 | Whitmore, III et al. | 600/459 |
| 5,944,023 | A | 8/1999 | Johnson et al. | 128/899 |
| 5,978,696 | A | 11/1999 | VomLehn et al. | 600/411 |
| 6,016,439 | A | 1/2000 | Acker | 600/411 |
| 6,019,724 | A * | 2/2000 | Gronningsaeter et al. | 600/439 |
| 6,036,682 | A | 3/2000 | Lange et al. | 604/529 |
| 6,073,043 | A | 6/2000 | Schneider | 600/424 |
| 6,097,978 | A | 8/2000 | Demarais et al. | 600/429 |
| 6,106,476 | A | 8/2000 | Corl et al. | 600/486 |
| 6,141,576 | A | 10/2000 | Littmann et al. | 600/381 |
| 6,188,355 | B1 | 2/2001 | Gilboa | 342/448 |
| 6,196,980 | B1 | 3/2001 | Akerfeldt et al. | 600/585 |
| 6,203,493 | B1 | 3/2001 | Ben-Haim | 600/117 |
| 6,203,543 | B1 | 3/2001 | Glossop | 606/60 |
| 6,205,411 | B1 | 3/2001 | DiGioia, III et al. | 703/11 |
| 6,210,339 | B1 | 4/2001 | Kiepen et al. | 600/486 |
| 6,216,029 | B1 | 4/2001 | Paltieli | 600/427 |
| 6,226,543 | B1 | 5/2001 | Gilboa et al. | 600/407 |
| 6,233,476 | B1 | 5/2001 | Strommer et al. | 600/424 |
| 6,235,038 | B1 | 5/2001 | Hunter et al. | 606/130 |
| 6,241,690 | B1 | 6/2001 | Burkett et al. | 600/585 |
| 6,272,370 | B1 | 8/2001 | Gillies et al. | 600/411 |
| 6,272,371 | B1 | 8/2001 | Shlomo | 600/424 |
| 6,285,898 | B1 | 9/2001 | Ben-Haim | 600/374 |
| 6,285,903 | B1 | 9/2001 | Rosenthal et al. | 600/433 |
| 6,288,785 | B1 | 9/2001 | Frantz et al. | 356/614 |
| 6,308,089 | B1 | 10/2001 | von der Ruhr et al. | 600/338 |
| 6,314,310 | B1 | 11/2001 | Ben-Haim et al. | 600/424 |
| 6,317,621 | B1 | 11/2001 | Graumann et al. | 600/424 |
| 6,332,089 | B1 | 12/2001 | Acker et al. | 600/424 |
| 6,336,906 | B1 | 1/2002 | Hammarstrom et al. | 600/585 |
| 6,356,783 | B1 | 3/2002 | Hubbard, Jr. | 600/546 |
| 6,380,732 | B1 | 4/2002 | Gilboa | 324/207.17 |
| 6,381,485 | B1 | 4/2002 | Hunter et al. | 600/407 |
| 6,383,174 | B1 | 5/2002 | Eder | 606/1 |
| 6,385,482 | B1 | 5/2002 | Boksberger et al. | 600/424 |
| 6,427,079 | B1 | 7/2002 | Schneider et al. | 600/424 |
| 6,442,417 | B1 | 8/2002 | Shahidi et al. | 600/429 |
| 6,468,265 | B1 | 10/2002 | Evans et al. | 606/1 |
| 6,473,635 | B1 | 10/2002 | Rasche | 600/428 |
| 6,484,118 | B1 | 11/2002 | Govari | 702/150 |
| 6,493,589 | B1 | 12/2002 | Medhkour et al. | 607/99 |
| 6,498,944 | B1 | 12/2002 | Ben-Haim et al. | 600/407 |
| 6,499,488 | B1 | 12/2002 | Hunter et al. | 128/899 |
| 6,500,114 | B1 | 12/2002 | Petitto et al. | 600/156 |
| 6,512,958 | B1 | 1/2003 | Swoyer et al. | 607/117 |
| 6,529,758 | B2 * | 3/2003 | Shahidi | 600/407 |
| 6,547,782 | B1 | 4/2003 | Taylor | 606/14 |
| 6,558,333 | B2 | 5/2003 | Gilboa et al. | 600/466 |
| 6,574,492 | B1 | 6/2003 | Ben-Haim et al. | 600/374 |
| 6,574,498 | B1 | 6/2003 | Gilboa | 600/424 |
| 6,580,938 | B1 | 6/2003 | Acker | 600/424 |
| 6,584,339 | B2 * | 6/2003 | Galloway et al. | 600/426 |
| 6,585,654 | B2 | 7/2003 | White et al. | 600/463 |
| 6,588,333 | B1 | 7/2003 | Homer et al. | 101/32 |
| 6,591,127 | B1 | 7/2003 | McKinnon | 600/411 |
| 6,591,129 | B1 | 7/2003 | Ben-Haim et al. | 600/424 |
| 6,593,884 | B1 | 7/2003 | Gilboa et al. | 342/448 |
| 6,615,155 | B2 | 9/2003 | Gilboa | 702/150 |

(56) References Cited

U.S. PATENT DOCUMENTS

| | | | |
|---|---|---|---|
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,386,339 B2 | 6/2008 | Strommer et al. | 600/424 |
| 7,925,328 B2 | 4/2011 | Urquhart et al. | |
| 8,046,052 B2 | 10/2011 | Verard et al. | |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031920 A1* | 10/2001 | Kaufman et al. | 600/431 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0099310 A1* | 7/2002 | Kimchy et al. | 600/424 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208122 A1 | 11/2003 | Melkent | |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0243147 A1* | 12/2004 | Lipow | 606/130 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0182319 A1 | 8/2005 | Glossop | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| BR | 9609484 | 12/1999 |
| CA | 2226938 | 2/1997 |
| DE | 69420228 D | 9/1999 |
| DE | 69420228 T | 4/2000 |
| EP | 0 845 959 | 6/1998 |
| EP | 0 654 244 | 8/1999 |
| IL | 0107523 | 1/2000 |
| IL | 0114610 | 7/2000 |
| JP | 2000500031 T | 1/2000 |
| WO | WO 97/03609 | 2/1997 |
| WO | 98/36684 A1 | 8/1998 |
| WO | WO 98/56295 | 12/1998 |
| WO | WO 00/22904 | 4/2000 |
| WO | 01/76497 A1 | 10/2001 |

OTHER PUBLICATIONS

TRA024—Knaan, Dotan, et al., Effective Intensity-Based 2D/3D Rigid Registration Between Fluoroscopic X-Ray and CT, *MICCAI*, vol. 1, 2003, pp. 351-358.

TRA025—Gee, A. H., et al., "3D Ultrasound Probe Calibration Without a Position Sensor", CUED/F-INFENG/TR 488, University of Cambridge, Department of Engineering, Sep. 2004, 21 pages.

TRA026—Lindseth, Frank, et al., "Probe Calibration for Freehand 3D Ultrasound Reconstruction and Surgical Navigation", Dec. 2002, 27 pages.

TRA027—Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

TRA028—Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

TRA001—Tanase, Dafina, et al., "Magnetic Sensors for Use on Guide Wires or Catheters", in *SeSens* 2001, in press 2002, pp. 868-872.

TRA002—Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

TRA003—Solomon, Stephen B., et al., "Real-Time Cardiac Catheter Navigation on Three-Dimensional CT Images", *Journal of Interventional Cardiac Electrophysiology*, vol. 8, 2003, pp. 27-36.

TRA004—Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

TRA005—Baert, Shirley A. M., et al., "Endpoint Localization in Guide Wire Tracking During Endovascular Interventions", *Academic Radiology*, vol. 10, No. 12, Dec. 2003, pp. 1424-1432.

TRA006—Baert, Shirley A. M., et al., "Three-Dimensional Guide-Wire Reconstruction from Biplane Image Sequences for Integrated

(56) References Cited

OTHER PUBLICATIONS

Display in 3-D Vasculature", *IEEE Transactions on Medical Imaging*, vol. 22, No. 10, Oct. 2003, pp. 1252-1258.
TRA007—Baert, Shirley A. M., et al., "Guide-Wire Tracking During Endovascular Interventions", *IEEE Transactions on Medical Imaging*, vol. 22, No. 8, Aug. 2003, pp. 965-972.
TRA008—Kobashi, Keiji, et al., "A New Biomechanical Model Based Approach on Brain Shift Compensation", *MICCAI* 2003, LNCS 2878, 2003, pp. 59-66.
TRA009—Timinger, Holger, et al., "Motion Compensation for Interventional Navigation on 3D Static Roadmaps Based on an Affine Model and Gating", *Physics in Medicine and Biology*, vol. 49, 2004, pp. 719-732.
TRA010—Lorigo, Liana M., et al., "Curves: Curve Evolution for Vessel Segmentation", *Medical Image Analysis*, vol. 5, 2001, pp. 195-206 (pp. 1-14).
TRA011—Chassat, Fabrice, et al., "Experimental Protocol of Accuracy Evaluation of 6-D Localizers for Computer-Integrated Surgery: Application to Four Optical Localizers", *MICCAI* 98, vol. 1496, Oct. 1998, Cambridge, Massachusetts U.S.A., p. 277-284.
TRA012—Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.
TRA013—"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.
TRA014—Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI* 2003, LNCS 2879, Publisher: Springer-Verlag Heidelberg, 2003, pp. 215-222.
TRA015—Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.
TRA016—SuperDimension, Ltd, web page, updated in Sep. 2005, 1 page.
TRA017—Schweikard, Achim, et al., "Robotic Motion Compensation for Respiratory Movement During Radiosurgery", *Computer Aided Surgery*, vol. 5, 2000, pp. 263-277.
TRA018—Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.
TRA019—Ellsmere, James, et al., "A Navigation System for Augmenting Laparoscopic Ultrasound", Center for Integration of Medicine and Innovative Technology, Cambridge, Massachusetts, 8 pages.
TRA020—Hofstetter, R., et al., "Fluoroscopy Based Surgical Navigation—Concept and Clinical Applications", Maurice E. Muller Institute for Biomechanics, University of Bern, Switzerland, 1997, 3 pages.
TRA021—Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.
TRA022—Summers, Ronald M., et al., "Colonic Polyps: Complementary Role of Computer-Aided Detection in CT Colonography", *Radiology*, vol. 225, No. 2, Nov. 2002, pp. 391-399.
TRA023—Hara, A. K., et al., "Reducing Data Size and Radiation Dose for CT Colonography", *AJR*, vol. 168, May 1997, pp. 1181-1184.
TRA029—RITA StarBurst Soft Tissue Access System and RITA StarBurst Hard Tissue Access System, http://www.ritamedical.com, Rita Medical Systems, Inc., copyright 2002, 8 pages.
TRA030—Cool-tip RF Tissue Ablation System, Cool-tip RF System, and Cool-tip Electrodes, http://www.valleylab.com/static/cooltip/products.html, Valleylab, copyright 2004, 4 pages.
TRA031—LeVeen Needle Electrode, Boston Scientific, printed from http://www.bostonscientific.com/med_specialty/deviceDetail.jhtml?task=_tskBasicDevice . . . , printed on Sep. 13, 2004, 1 page.
TRA032—Bradford J. Wood et al., "Navigation with Electromagnetic Tracking for Interventional Radiology Procedures: A Feasibility Study", Laboratory Investigations, *Journal of Vasc.Interv. Radiol.*, vol. 16, 2005, pp. 493-505.

\* cited by examiner

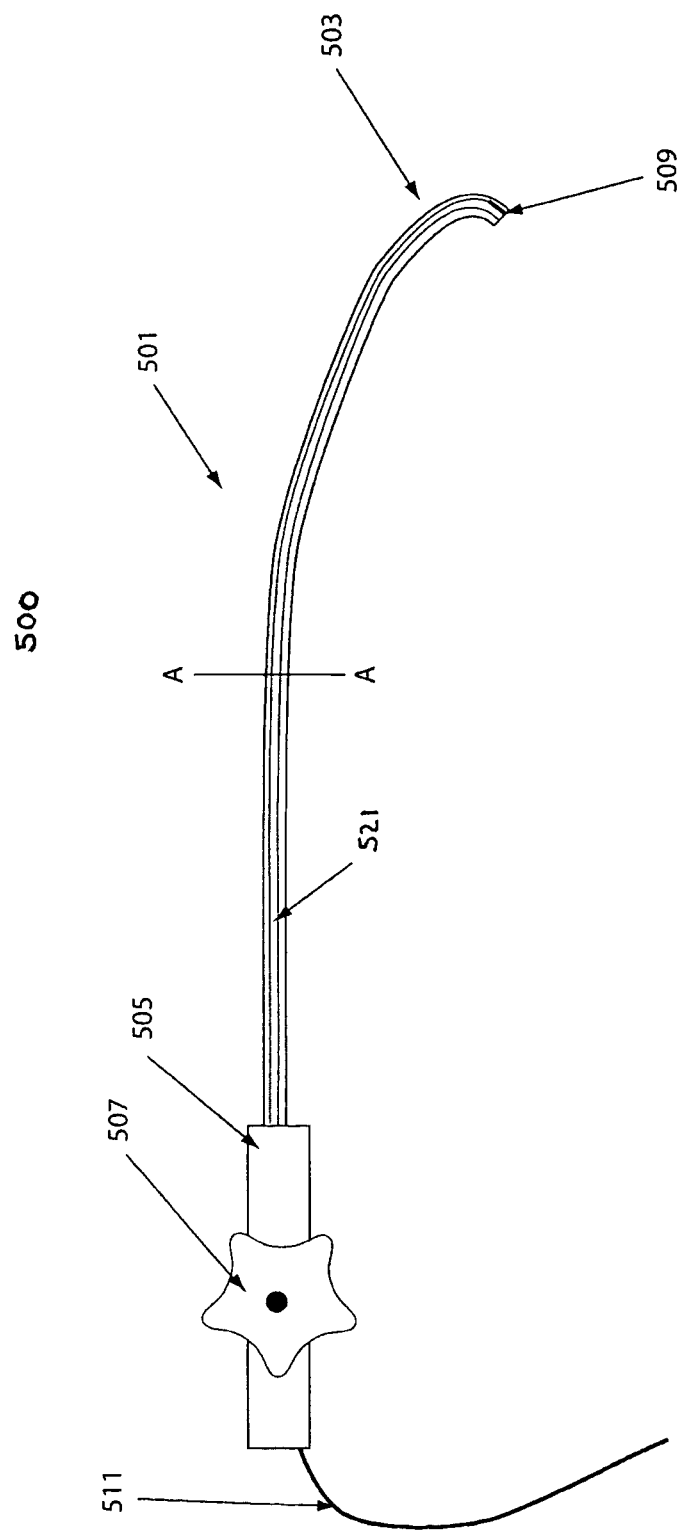

SYSTEM, METHOD AND DEVICES FOR NAVIGATED FLEXIBLE ENDOSCOPY

REFERENCE TO RELATED APPLICATIONS

This application claims priority to U.S. Provisional Patent Application No. 60/710,657, filed Aug. 24, 2005, which is hereby incorporated by reference herein in its entirety.

FIELD OF THE INVENTION

The present invention relates to methods and apparatus for assisting navigated flexible endoscopy.

BACKGROUND

During exploratory endoscopic procedures such as colonoscopy, bronchoscopy, endoscopic retrograde cholangiopancreatography (ECRP) or other endoscopic procedures, it is desirable to locate any lesions or other areas that are of interest such as, for example, precancerous changes, bleeding sites, polyps, nodules, or other areas of interest. Traditional endoscopic examination consists entirely of an optical examination of the conduit or area of interest within the anatomy of the patient. More recently, virtual examination has become more popular. In virtual endoscopy, computerized tomography (CT), magnetic resonance (MR), ultrasound, or other diagnostic imaging methods are first used to locate a suspect lesion either with or without the assistance of a computer algorithm (e.g., "CAD" or computer assisted diagnosis). Lesion candidates are then inspected optically and treated or biopsied as deemed appropriate by the physician.

During optical endoscopic examination, it is important to locate all flagged suspicious regions (e.g., lesions or other areas of interest) and examine them. In practice, this can be difficult because there is no way to easily register image-based data regarding suspect lesions to the patient space (e.g., the real world location of the suspected lesions). Often the length of the endoscope from the insertion point into the patient is the only indication of the location of suspect lesions. Typically this indication is extremely crude, averaging 10 centimeters (cm) or more of error. In arborized tissues, such as, the bronchial pathways of the lungs, physicians frequently become disoriented and enter a branch other than the desired one.

The invention is designed to assist in the optical localization of suspect lesions or other areas of interest that are initially detected using virtual colonoscopy or other virtual endoscopy. This invention enables the physician performing the examination to more efficiently locate suspicious lesion candidates from imaging scans, such as CT, MR, ultrasound, or other imaging scans. Once the position of the candidate lesion or other area of interest is determined from the imaging scan (either manually, computer assisted, or through the use of a fully automated CAD software) the (x, y, z) location of the candidate will be recorded in image (i.e. CT space) or in some other convenient form. The system then enables these locations to be indicated to the physician during a conventional optical endoscopic exam, increasing the likelihood that he will be able to locate and inspect them. The invention further enables the shape of a flexible endoscope or other instrument to be determined without the use of additional imaging.

SUMMARY OF THE INVENTION

In one embodiment, the invention provides a system and method for performing and/or assisting in image-guided medical endoscopic medical procedures. In one embodiment, the system of the invention may comprise a control unit, a control application, a tracked medical instrument, a position sensing system, a display device, and/or other elements.

In one embodiment, the control unit may include one or more special purpose or general purpose computers and/or processors cable of responding to and executing instructions in a defined manner. The control unit may include, be associated with, and/or be in communication with a memory device that stores any data necessary for the performing the features or functions of the invention such as, for example, image data, position data, orientation data, coordinate data, transformation matrices, and/or other data. The control unit may also include, run, and/or support a control application comprising one or more software modules for directing and performing one or more data reception, transmission, data processing, and/or other data manipulation operations according to the features and functions of the invention. Other software modules may also be utilized with the system of the invention.

In one embodiment, the tracked medical instrument may include an endoscope equipped with at least one working channel, optics for viewing the anatomy present at the distal tip of the endoscope, one or more trackable sensor elements, and/or other elements. The position and/or orientation of the one or more sensor elements may be determined/monitored by the position sensing system. The position sensing system may be in communication with the control unit and may provide sampled position coordinates and orientation information of the one or more sensor elements to the control unit. An example of the position sensing system is an electromagnetic position sensing system used with electromagnetic sensor elements.

In some embodiments, the tracked medical instrument may include an untracked endoscope or other instrument used in conjunction with a tracked catheter, tracked guidewire, tracked treatment device, and/or other tracked instrument. In some embodiments, the tracked medical instrument may be a tracked endoscope. In some embodiments, the system of the invention may not include an endoscope, but may include one or more tracked devices that do not include the optics typically associated with an endoscope.

The system of the invention may also include a display device that displays images used in the system and methods of the invention such as, pre-operative images of the anatomy of a patient (including one or more items of interest), intra-operative images of the anatomy of the patient (including an inserted medical instrument and the one or more items of interest), real-time or near-real-time images displaying motion of the tracked instrument relative to the one or more items of interest within the anatomy of the patient, and/or other images or data.

In one embodiment, the invention provides a method for performing and/or assisting with an image-guided medical procedure, wherein a path of the tracked medical instrument in image space is registered to the path of the medical instrument in patient space. The path of the medical instrument in image space may be obtained from one or more pre-operative images and/or one or more intra-operative images of the anatomy of the patient. The path of the medical instrument in patient space may be obtained using a position sensing system and one or more sensor elements located on the medical instrument itself or on a separate tracked instrument. The patient space data is then registered to the image space data to produce a registration matrix relating the patient space to the image space. This registration matrix may be used to display the location and movement of the medical instrument on the one or more pre or intra-operative images so as to navigate to the one or more items of interest within the anatomy of the patient.

In one embodiment, the method of the invention includes obtaining one or more pre-operative images of a portion of the anatomy of a patient, wherein the portion of the anatomy of the patient includes the one or more items of interest. For example, if the medical procedure was a colonoscopy for the investigation of one or more colonic lesions, the one or more pre-operative images may be taken of the colon and/or digestive tract of the patient. The pre-operative images may comprise image data obtained using, x-rays, computerized tomography (CT), magnetic resonance (MR), positron emission tomography (PET), ultrasound, and/or other imaging modalities.

In one embodiment, the pre-operative image data is then examined to determine the locations of candidate lesions or other items or points of interest in the patient's anatomy. In one embodiment, these locations are expressed in the coordinate system of the pre-operative imaging modality (i.e. the "pre-operative image space"). As such, the location of all lesions or items of interest is expressed in terms of a frame of reference intrinsic to the pre-operative image-gathering device.

In some embodiments, this examination may be performed by a physician, technician, or other individual. In other embodiments, the examination may be partially assisted by diagnostic software modules (e.g., one or more modules comprising the control application). In still other embodiments, this examination may be completely automated using one or more software modules or applications.

In one embodiment, such as, when the anatomy involved in the medical procedure includes a channel-like organ or region (e.g., the colon, bronchial system, or other channel-like region) the centerline of a path through the anatomy/organ may calculated. For example, if the anatomy on which the procedure is performed is the patient's colon, the centerline may be calculated and represented by a locus of points that form a path defining the approximate centerline of the colon. Because these coordinates are derived from the one or more pre-operative images, these coordinates are expressed relative to the pre-operative image space.

In one embodiment, a skeleton or "graph" of a pathway to the organ may also be determined. This may be particularly useful if the conduit/organ in which the items of interest are located is arborized (e.g., bronchial passages). The graph represents a map from start to target (e.g., a lesion or other item of interest) along the centerline of any branches in the organ (e.g., the bronchi of a lung) indicating the direct path to the target, including all turns.

In another embodiment, rather than a calculated centerline, the "most likely path" of the passage of a flexible endoscope or other flexible instrument is calculated using the one or more pre-operative images. The coordinates of a plurality of points defining this "most likely path" are determined in the pre-operative image space. In some instances, the most likely path of an endoscope may include points that intersect the walls of any conduit-like anatomy in the anatomical region (e.g., the endoscope may collide with the walls of the colon), rather than points that follow a centerline path through the anatomy. Using mathematical predictive techniques, this "most likely path" of an endoscope/instrument can be calculated. In some embodiments, determination of the most likely path uses a predictive collision detection system that predicts the endoscope locations touching the walls of channel-like anatomy such as, for example, at locations with sharp curvature (e.g., the junction between the ascending-transverse and transverse-descending colon). In some embodiments, this predicted path may also be measured, as discussed below.

In one embodiment, the medical procedure may begin, usually by insertion of the medical instrument. For example, if the medical procedure included a colonoscopy, the medical procedure may include insertion of a colonoscope or other endoscope into the colon of the patient. The medical instrument may be inserted into the anatomy of interest in a manner known in the art. In some embodiments, this can be done by inserting the instrument into natural or artificially created orifice of the patient.

In some embodiments, wherein the endoscope and/or other medical instrument is visible to an imaging modality, intra-operative images of the anatomy of the patient may be taken with the endoscope inserted. The intra-operative imaging may be used to precisely determine the location of the path of the endoscope and/or other instrument following insertion. For example, in one embodiment, the path of the endoscope can be obtained using two or more fluoroscopic shots taken at different angles, a CT scan, ultrasound images, or other images taken following insertion of the endoscope. This intra-operative imaging may also be used to determine the location of the lesions or other areas of interest relative to the inserted endoscope.

In general, the intra-operative images may be obtained in a new coordinate system/frame of reference (i.e., "intra-operative image space"). In some embodiments, as discussed herein, the path of the endoscope determined using the intra-operative images may be matched or registered with the coordinate system of the pre-operative images on which the candidate lesions, or other items of interest have been annotated, and on which the predicted path of the endoscope (e.g., centerline path or most likely path) has been calculated.

The centerline path and/or the most likely path of the endoscope calculated in the pre-operative image space may differ from the actual path taken by the inserted endoscope. As such, the intra-operative images provide the "true path" of the endoscope. The true path of endoscope becomes available once the intra-operative imaging is performed and analyzed. Registering the intra-operative image data with the pre-operative image data provides a more accurate set of image space data regarding the path of the endoscope and provides a richer set of data regarding other features of the anatomy of the patient.

In some embodiments, it may be desirable to determine the contortions that the endoscope or other instrument has undergone without the use of images. For example, a colonoscope frequently undergoes loops and other deformations that affect a medical procedure being performed with the colonocscope. Normally, it is difficult to determine these deformations without imaging. If a tracked elongated member is dragged through a channel of the endoscope or other instrument, the locus of points gathered as the position of sensor elements in the tracked member are sampled prescribe a shape that is the same as the shape of the endoscope or other instrument. This information may be used to assist in the medical procedure. In some embodiments, only a single sensor element attached to a slidable elongated member (e.g., a guidewire) is needed to determine this shape. In some embodiments, multiple sensor elements may be fixed to or moved along the endoscope or other instrument to determine its path. In some embodiments, motion may be compensated for by using a dynamic reference device such as, for example, a skin motion tracker, an internally-placed catheter, or other dynamic referencing device. Motion may also be compensated for using a gating device such as, for example, an ECG (electroencephalogram), a respiratory gating device, or other gating device.

To conduct or assist image-guided surgery, it is desirable to register or match the coordinate system of the position sensing system to the coordinate system belonging to the pre-operative image space, intra-operative image space, or a co-registered combination of the pre and intra-operative images. One way of facilitating this is by acquiring a plurality of points in position sensor space or "patient space" (i.e., the coordinate system/frame of reference intrinsic to the position sensing system) and mathematically matching them to the same points in image space.

This may be done by first obtaining patient space data regarding the endoscope or other instrument within the anatomy of the patient. This patient space data may be obtained using the position sensing system and the one or more sensor elements located on the endoscope or other medical instrument.

The position sensing system is associated with its own coordinate system (i.e., a frame of reference intrinsic to the position sensing system). The position sensing system is capable of determining the position and orientation of one or more sensor elements attached to an instrument (e.g., the endoscope or another instrument) and relaying that information to the control unit.

Acquisition of data in patient space can be performed by dragging a tracked endoscope or other instrument back through the anatomy of the patient (e.g., dragging it back through the colon) or a tracked instrument back through the working channel of the endoscope (or the working channel of a catheter or other instrument inserted into the patient's anatomy) while the position sensing system gathers/samples data points regarding the position and/or orientation of the sensor elements on the tracked instrument in the frame of reference/coordinate system of the position sensing system. This technique may be labeled a "dragback" technique. More information regarding the use of this technique and other information relevant to registration, dynamic referencing, and other image guided surgery techniques can be found in U.S. patent application Ser. No. 11/059,336 (U.S. Patent Publication No. 20050182319), which is hereby incorporated by reference herein in its entirety.

In some embodiments, instead of, or in addition to, using the dragback method described above for obtaining data points in patient space, individual identifiable locations in the anatomy of the patient are sampled by touching or indicating them with the tracked instrument or endoscope. In some embodiments, a tracked instrument may be temporarily secured in the endoscope and sensor element positions sampled (i.e., not dragged through the endoscope). In some embodiments, a tracked ultrasound device may be used to indicate points.

In one embodiment, registration of the patient space data to the image space data may involve only image space data acquired pre-operatively. For example, in one embodiment, the patient space path of the endoscope acquired using a tracked instrument and the position sensing system may be registered to pre-operative image space data relating to the "assumed" path of the endoscope (i.e. based on the centerline path or the "most likely path" calculated using the pre-operative images).

In some embodiments, however, the patient space data may be registered to the intra-operative image space data. For example, the image space path of the endoscope registered to the patient space data may be based on the directly measured path of the inserted endoscope observed in the intra-operative images (e.g., the "true path"). Directly measured or true paths may require a method expressing the coordinates of this path in the same frame of reference as the candidate lesions (e.g., the above-discussed co-registration of the pre-operative images to the intra-operative images). In these embodiments, a separate registration must be performed to match the pre-operative images to the intra-operative images before the combined image data is registered to the patient space data. In one embodiment, this is done by using 2D-3D or 3D-3D co-registration techniques.

Once at least two representations of the endoscope's path have been determined (i.e. in image space [pre-operative and/or intra-operative] and in patient space), they may be "matched" or "registered". The two paths may be matched using an iterative closest points (ICP), piecewise ICP, or similar algorithm. This enables a registration matrix (or sequence of registration matrices) to be generated. In some embodiments, the registration takes the form of a rigid transformation matrix. In some embodiments, the registration uses an affine transformation. In some embodiments, several matrices are used at different places. In some embodiments, weighted combinations of matrices are used. In some embodiments, complex matrices embodying deformable transformations are used.

In some embodiments, registration may be accomplished using techniques other than or in addition to the dragback technique described above. For example, in one embodiment, a "landmark-based" method may be used that includes the identification of "fiducials" present in both pre-operative images and identified during the examination by, for example, touching them with a tracked instrument or imaging them with a tracked calibrated ultrasound transducer to determine their location in patient space. If at least 3 such points are co-located, a registration can be performed using techniques such as the ICP above or simpler methods such as singular valued decomposition. In some embodiments, the fiducials can be naturally occurring landmarks, such as polyps, and in other embodiments, they can be artificial landmarks such as small balls, surgical staples, specially placed needles, or other elements that may be visible in both the pre-operative images and intra-operative images. Other registration methods may also be used.

In some embodiments, the endoscope or other elongated instrument may be equipped with additional sensor elements that can act as dynamic referencing or tracking sensors, either with multiple sensor elements placed along the scope or one or two sensor elements located at the most distal end of the scope. These track gross patient movement or the motion of the field generator of the position sensor system as long as the endoscope or other elongated instrument remains stationary.

In some embodiments, dynamic references (i.e., sensor elements) can be placed into additional catheters, guidewires, or instrument placed elsewhere in/on the patient that are not affected by the exam. The purpose of these sensor elements is to account for patient movement, including that occurring from respiration, or other patient movement.

Once registration has been performed, the invention may include a navigation step in which the endoscope or other instrument equipped with sensor elements is tracked by the position sensing system. As the endoscope is moved through the anatomy to inspect its interior, the position of the endoscope or tracked instrument may be sampled in the reference frame of the position sensing system. The locations and orientations determined by the position sensing system are sent to the control unit, which creates a real-time or near real-time display of the motion of the tracked instrument relative to the lesions or other points of interest as identified in the image space. The display is enabled by the transformation matrix produced by the registration. This display is used, for example, for image-guided navigation of the endoscope in an attempt to locate suspect lesions or other items of interest using the optics of the endoscope.

In some embodiments, the only information required may be the shape of the endoscope or other instrument. This may be acquired without having to explicitly perform a registration step.

In some embodiments, whenever one of the flagged locations (i.e., lesions or other items of interest) is in the proximity of the tracked portion of the endoscope or other instrument, the physician may be notified or he or she will be able to determine from the images that he or she is in proximity of the suspect lesion and can look for it.

In some embodiments, the lesions or other items of interest can then be treated, destroyed, biopsied, or otherwise treated, if detected. This treatment may be enabled by treatment-oriented instruments, that may be tracked themselves, and which may be inserted through the working channel of the endoscope that has been navigated to a lesion or other item of interest.

In some embodiments, the sensor elements on a trackable guidewire act simply as a distance measurement device to determine the location of the endoscope relative to a known location. In this embodiment, the relative location of all suspect lesions are calculated relative to each other and landmarks within the anatomy. As each is examined, the location is stored and the distance to the next location of interest is calculated. In this way, the system is self-correcting at each identified location along the path of the endoscope as it is removed. This method may not require registration to be performed prior to use.

For example, during a "virtual colonoscopy," suspect lesions may be flagged (on the preoperative images) by the physician or computer program, and their locations calculated in the frame of reference of the images.

During the intervention, the colonoscope is inserted into the colon and a reference point is identified (for example, the ileocecal sphincter or appendiceal orifice). The path length of each of the suspect lesions is identified relative to this location along the centerline of the colon. For a first lesion, the path is the length of the distance along the centerline of the colon between the reference point (e.g., the appeniceal orifice) and the first suspect lesion. Likewise, the path length of a second lesion is the length of the distance along the centerline between the reference point (e.g., the appeniceal orifice) and the second suspect lesion. Thus by dragging the endoscope back and calculating the distance traversed by the sensor attached to the endoscope, the location of the next suspect lesion can be determined.

Once the first lesion is encountered, the locations of the next lesions may be calculated relative to it. For example, the second suspect lesion can be estimated to be located a distance from the first lesion (or equivalently a distance from the appeniceal orifice). In general it may be more accurate to estimate measure the inter-lesion distances, rather than the distance between the start point and each lesion.

In one embodiment, the physician indicates each lesion as it is encountered and in one embodiment, the lesions and landmarks are weighted according to their distance from the reference point.

In one embodiment, these measured distances are augmented using shape information regarding the endoscope or other instrument, as may be determined using a path determination method such as those described herein. This shape information may be helpful in more accurately determining the location of an area of interest.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

BRIEF DESCRIPTION OF THE DRAWINGS

FIGS. 5A and 5B illustrate an example of a steerable catheter, according to an embodiment of the invention.

DETAILED DESCRIPTION

Figure 1:
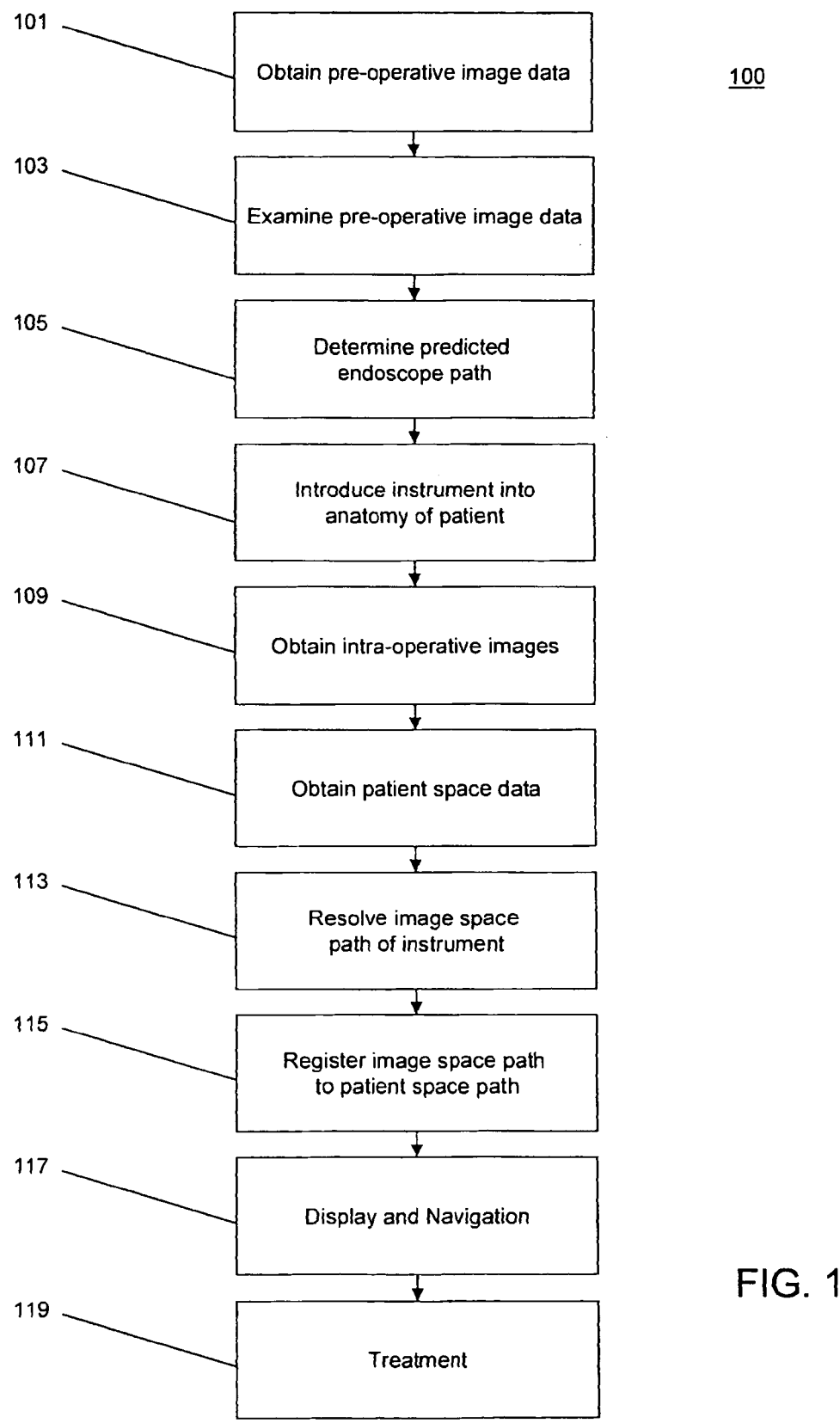
FIG. 1 illustrates an example of a process for assisting an image-guided endoscopic procedure, according to an embodiment of the invention.

In one embodiment, the invention provides method for assisting an image-guided endoscopic procedure. FIG. 1 illustrates a process 100, an example of a method for assisting an image-guided endoscopic medical procedure. In an operation 101, a conventional virtual endoscopic data set may be acquired prior to commencement of the medical procedure using existing standard protocols such as, for example, those described in A. K. Hara et al., *Reducing Data Size and Radiation Dose for CT Colonography*, 168 American Journal of Roentgenology 1181-1184 (1997), which is hereby incorporated by reference herein in its entirety.

The virtual endoscopic data set may comprise image data obtained using x-rays, computerized tomography (CT), magnetic resonance (MR), positron emission tomography (PET), ultrasound, and/or other imaging modalities. In some embodiments, the pre-operative imaging may be performed with the patient in same position as the endoscopic procedure. In some embodiments the endoscopic procedure occurs in the same room as the pre-operative imaging.

In an operation 103, the pre-operative image data may then by examined by a physician, technician, or other individual. In some embodiments, this examination may include the assistance of computer assisted diagnostic software such as, for example, that described in Ronald M. Summers et al., *Colonic Polyps: Complementary Role of Computer-aided Detection in CT Colonography*, 225 Radiology 391-399 (2002), which is hereby incorporated by reference herein in its entirety. In some embodiments, this examination may be completely automated using one or more software modules or applications.

During the examination of operation 103, the locations of candidate lesions or other items or points of interest in the patient's anatomy are determined. In one embodiment, these locations are expressed in the coordinate system of the pre-operative images (i.e. "pre-operative image space"). As such, the location of all lesions or items of interest is expressed in terms of a frame of reference intrinsic to the pre-operative image-gathering device.

Figure 2:
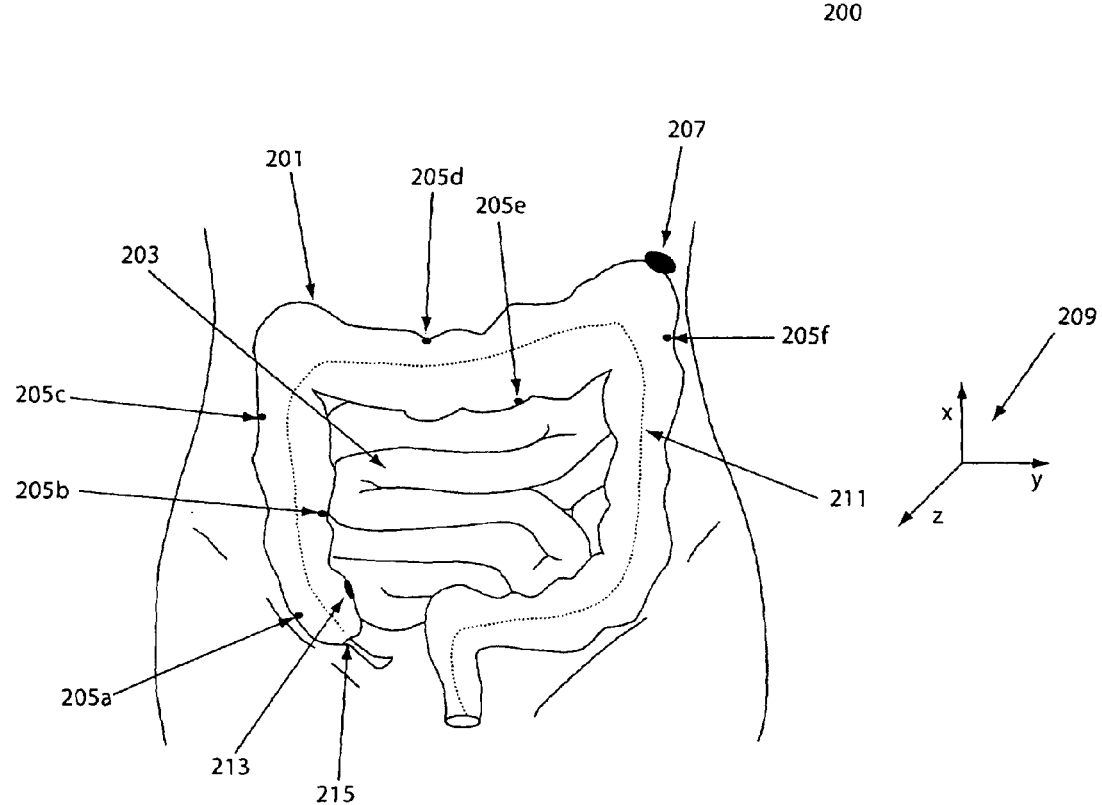
FIG. 2 illustrates an example of a pre-operative image of a portion of an anatomy of a patient, according to an embodiment of the invention.

FIG. 2 illustrates an example image 200 of a part of an anatomy of a patient, including colon 201 and small intestine 203. Identified candidate lesions are indicated as 205a, 205b, 205c, 205d, 205e, and 205f. A region of interest is indicated as 207. All identified lesions, regions, or other points or items of interest are expressed in terms of a coordinate system 209 that is a frame of reference intrinsic to the image gathering device used to produce image 200.

In an operation 105, a predicted path of a flexible endoscope or other instrument through the anatomy of the patient wherein the one or more points of interest reside is determined. For example, in one embodiment, the centerline of a path through the patient's anatomy is obtained. For instance, if the anatomy on which the procedure is performed is a channel-like organ or region (e.g. the colon, bronchial system, or other channel-like region), the predicted path of a flexible endoscope may comprise a locus of points that form a path defining the approximate centerline of the organ. The coordinates of these points are determined in the pre-operative image space. Image 200 of FIG. 2 illustrates calculated centerline 211 through colon 201.

In another embodiment, rather than a calculated centerline, the predicted path of the endoscope comprises a "most likely path" of the passage of a flexible endoscope that is charted on the pre-operative images. The coordinates of a plurality of points defining this "most likely path" are determined in the pre-operative image space. In some instances, the most likely path of an endoscope may include points that intersect or collide with the walls of the patient's anatomy, rather than points that follow a centerline path through the anatomy. Using mathematical predictive techniques, this "most likely path" of an endoscope can be assumed. In some embodiments, determination of the most likely path uses a predictive collision detection system that predicts an endoscope location that touches the walls of channel-like anatomy at locations with sharp curvature such as, for example, the junction between the ascending-transverse and transverse-descending colon.

Figure 3:
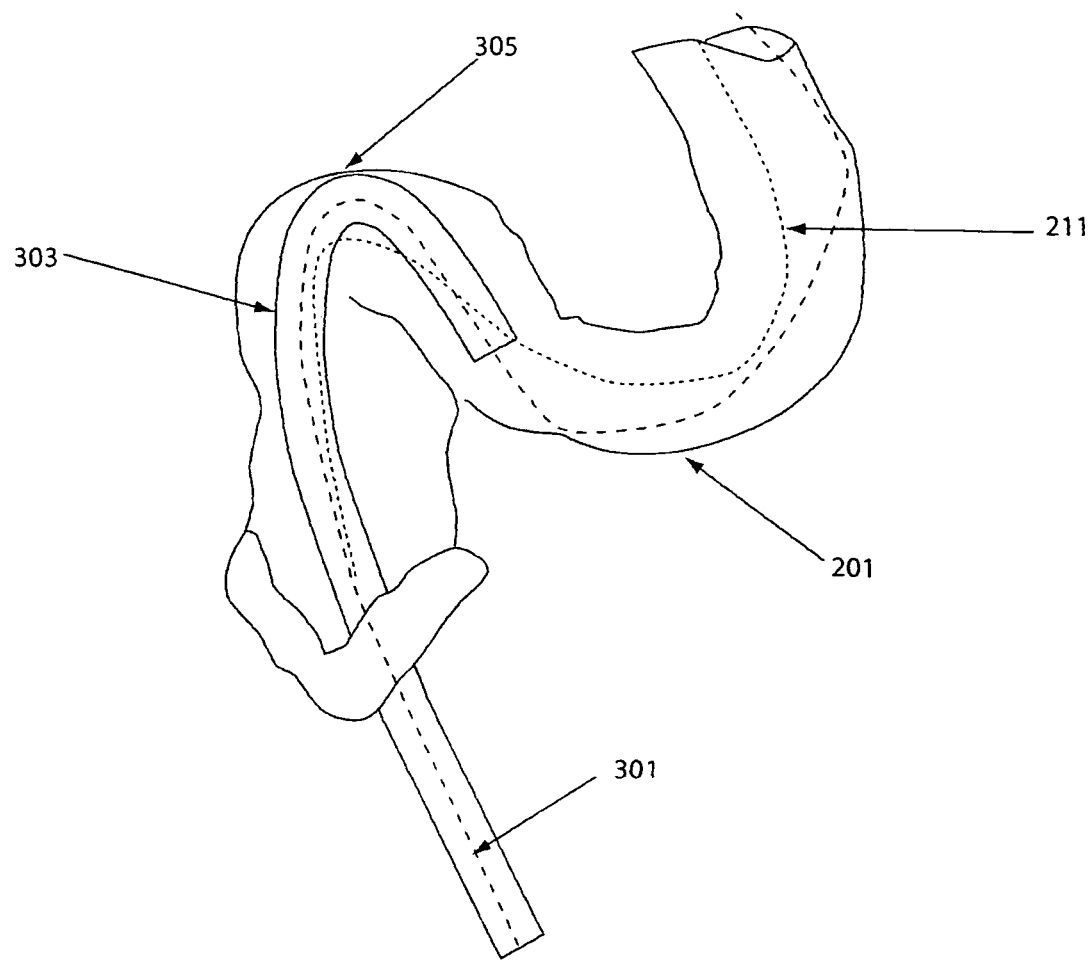
FIG. 3 illustrates an example of the "most likely path" of an endoscope through a conduit, according to an embodiment of the invention.

FIG. 3 illustrates a portion of colon 201, wherein a predicted "most likely path" of an endoscope is indicated as path 301. An endoscope 303 is shown along part of most likely path 301. Endoscope 303, as illustrated, collides with the wall of colon 201 at location 305. Rather than follow the path of centerline 211, endoscope 303 is most likely to follow path 301.

In some embodiments, during operations 103 and/or 105, one or more anatomical points of interest may also be noted and their coordinates in pre-operative image space may be determined. For example, as illustrated in image 200 of FIG. 2, if the anatomy of the patient upon which the medical procedure is being performed includes colon 201, the location of ileocecal sphincter 213, appendiceal orifice 215, or other anatomical points of interest may be noted and/or their positions in the image space may be determined.

In one embodiment of the invention, the patient undergoes an optical endoscopic examination or other medical procedure using traditional endoscopic techniques and/or instruments augmented with one or more sensor elements, as described herein.

Figure 4A:
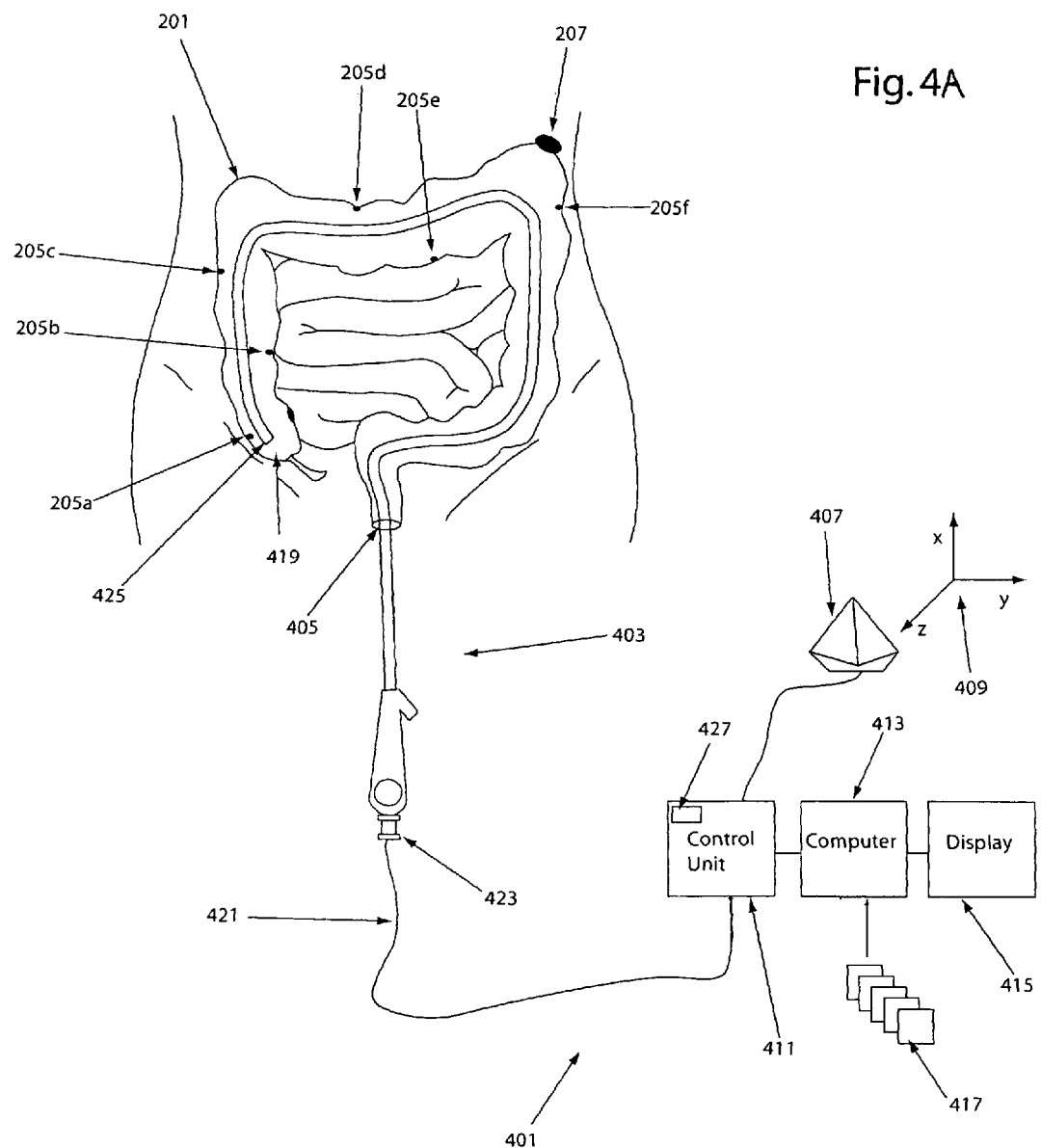
FIG. 4A illustrates an example of a system for image-guided endoscopy used in the anatomy of a patient, according to an embodiment of the invention.

FIG. 4A illustrates a portion of the anatomy of a patient, including colon 201, and a system 401 for performing an image guided medical procedure. FIG. 4A illustrates candidate lesions 205a-205f and region of interest 207. Flexible endoscope 403, which is part of system 401, is shown inserted into colon 201 via orifice 405. One of ordinary skill in the art will recognize that, while the figures illustrate the invention as used in colonoscopy, these applications are illustrative only, and applications of the systems and methods described herein on other parts of the anatomy of a patient are within the scope of the invention, including those with additional, modified, and/or alternate system components. As such, flexible endoscope 403 may comprise a colonoscope, a bronchoscope, a ventricularscope, a cystoscope, a arthroscope, a duodenoscope, a colposcope, a hysteroscope, a laparoscope; a laryngoscope, a sigmoidoscope, a gastroscope, or other instrument.

According to one embodiment of the invention, a position sensing system 407 is used during the endoscopic medical procedure. As such, position sensing system 407 may be located near, on, or in the patient. Position sensing system 407 is associated with its own coordinate system 409 (i.e., a frame of reference intrinsic to position sensing system 407). Position sensing system 407 is capable of determining the position and orientation of a sensor element attached to an instrument (e.g., endoscope 403) and relaying that information to an attached control unit 411. Control unit 411 may in turn be connected to a computer system 413 onto which pre-operative images, intra-operative images, other images, coordinates of the candidate lesions, centerline path points, most likely path points, regions of interest, and/or other data 417 is loaded. Computer system 413 may be associated with a display device 415, input devices (not shown), and/or other devices.

In one embodiment, control unit 411 may be attached directly (e.g., via a wired connection) to a sensor element embedded in endoscope 403 or other tracked instrument. In other embodiments, control unit 411 may be in communication with the sensor element via a wireless connection. In one embodiment, the sensor element may comprise an electromagnetic sensor coil. In these embodiments position-sensing system 407 may comprise an electromagnetic position sensing system that is capable of determining the position and orientation of the electromagnetic sensor coil and/or other electromagnetic sensor coils. Other types of position sensing systems may be used.

Referring back to FIG. 1, in an operation 107, the medical procedure may begin by introducing an instrument into the anatomy of the patient. For example, operation 107 may include inserting endoscope 403 into colon 201 in a manner known in the art. In some embodiments, this can be done by inserting endoscope 403 into natural or artificially created orifice of the patient (e.g. orifice 405).

In some types of standard endoscopy as known in the art, the medical procedure may include fully inserting endoscope 403 into the anatomy of interest of the patient and then slowly withdrawing it from the anatomy while observing optically in all directions. For example, in the case of colonoscopy, endoscope 403 may be fully inserted, e.g., to caecum 419 and then withdrawn while optically observing the interior of colon 201.

In some embodiments, once the endoscope is fully inserted in the organ (or inserted to a desired depth), a guidewire, catheter, biopsy device, diagnostic tool or other elongated instrument 421, may be placed inside endoscope 403's working channel 423. In some embodiments, the distal end of elongated instrument 421 is moved through working channel 423 of endoscope 403 to or beyond a distal end 425 of endoscope 403. In some embodiments, elongated instrument 421 may be placed beside the optical portion of endoscope 403.

Figure 4B:
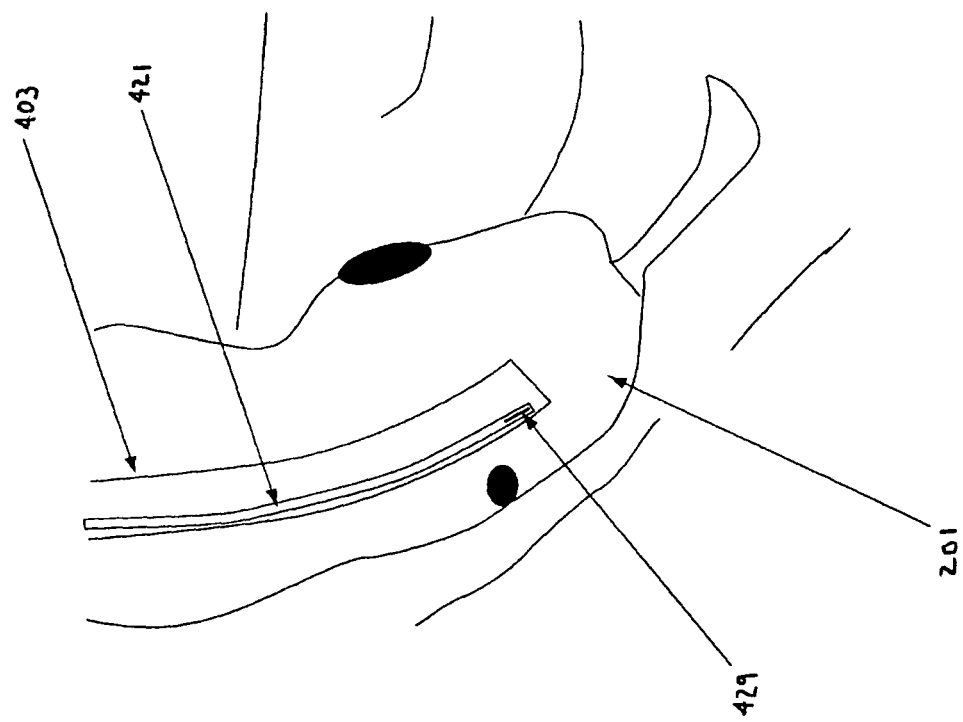
FIG. 4B illustrates an example of a tracked elongated instrument within an endoscope used in the anatomy of a patient, according to an embodiment of the invention.

In one embodiment, such as those illustrated in FIG. 4B, elongated instrument 421 may be equipped with at least one sensor element 429, which enables the determination of the position and/or the orientation (in the frame of reference 409 of position sensing system 407) of a specific part of elongated instrument 421 and therefore the part of endoscope 403 in which the specific part of elongated instrument 421 resides. In one embodiment, sensor element 429 may be placed at the tip of elongated instrument 421. For more information regarding instruments equipped with sensor elements and other information relevant to the invention, see U.S. patent application Ser. No. 11/471,604, entitled "System, Method and Apparatus for Navigated Therapy and Diagnosis, which is hereby incorporated by reference herein in its entirety.

In some embodiments, one or more sensor elements may be embedded in or attached to endoscope 403 itself. Sensor elements embedded directly in endoscope 403 enable direct determination of the position and orientation of the tip (i.e., distal end 425) of endoscope (when at least one sensor element is located at or near the tip of the endoscope) and potentially many points along endoscope 403 (when multiple sensor elements are located along a portion of the endoscope), and thus its "shape" within the anatomy of the patient, in the frame of reference of position sensing system 407. Sensor elements in endoscope 403 may be used instead of, or in addition to, an elongated instrument 421 with one or more sensor elements included therein.

In one embodiment, endoscope 403 is a flexible endoscope. For example, endoscope 403 may comprise a colonoscope or other endoscope designed to examine the digestive system. As discussed herein, other types of endoscopes may be used. In some embodiments, endoscope 403 can be replaced by an elongated member such as a catheter that contains a working channel.

In some embodiments, wherein endoscope 403 and/or elongated instrument 421 is visible to an imaging modality, supplementary or "intra-operative" images of the anatomy of the patient may be taken in an operation 109, with endoscope 403 inserted. The imaging modality used may be considered a "secondary" or "intra-operative" imaging modality relative to the imaging modality used to acquire the pre-operative images, which may be considered a "primary" or pre-operative imaging modality. In some embodiments, the primary and secondary imaging modalities may be the same or similar. In some embodiments, because the relative position of the patient and the imaging modality used in imaging may differ from pre-operative imaging and intra-operative imaging, the coordinate systems of the pre-operative images and the intra-operative images may differ, even when the imaging modalities are the same.

In some embodiments, as more complex imaging modalities (e.g., CT or MR scans) may be difficult or unwieldy to use during the endoscopic procedure, x-ray, fluoroscopic ultrasound, or other easier to use imaging devices may be used for intra-operative imaging. However, CT, MR, or other complex imaging may be used, nonetheless.

The intra-operative imaging may be used to precisely determine the location of the actual path of endoscope 403 following insertion. For example, in one embodiment, the actual path of endoscope 403 can be obtained using two or more fluoroscopic shots taken at different angles, a CT scan, or other images taken following insertion of endoscope 403. This intra-operative imaging may also be used to determine the location of the lesions 205a-205f or other areas of interest relative to the inserted endoscope.

In general, the intra-operative images may be obtained in a new coordinate system belonging to the secondary imaging modality (e.g., in a frame of reference relative to the secondary imaging modality). The actual path of endoscope 403 determined using the intra-operative images may, in one embodiment, be matched or registered to coordinate system 209 of the pre-operative images on which the candidate lesions 205a-205f or other items of interest have been annotated. For example, in one embodiment, centerline path 211 calculated above for endoscope 403 may differ from the actual path taken by inserted endoscope 403 (i.e., the "true path" of the endoscope). The true path of endoscope 403 becomes available once the intra-operative imaging is performed and analyzed.

In some embodiments it is desirable to register or match the coordinate system of position sensing system 407 to one or more of the coordinate system belonging to the primary imaging modality (e.g., coordinate system 209) and/or the coordinate system belonging to the secondary imaging modality (not illustrated). One way of facilitating this is by acquiring a plurality of points in position sensor space (i.e., coordinate system 409—the frame of reference intrinsic to position sensing system 407) and mathematically matching them to the same points in image space of the pre-operative images (i.e., coordinate system 209—the frame of reference of the primary imaging modality). As such, in an operation 111, data regarding a plurality of points in position sensor space may be obtained using one or more sensor elements and position sensing system 407.

Acquisition of data in position sensor space can be performed by obtaining the path of endoscope 403 by, for example, sampling sensor elements placed in endoscope 403 using position sensing system 407 to determine the path of endoscope 409. Another method may involve dragging a tracked endoscope (e.g., endoscope 409) back through the anatomy of the patient (e.g., dragging it back through colon 201) or elongated instrument 421 back through working channel 423 of endoscope 403 (or the working channel of a catheter or other instrument inserted into the patient's anatomy) while position sensing system 407 gathers data points regarding the position and/or orientation of the sensor elements on the tracked instrument in coordinate system 409 of position sensing system 407. While the frame of reference/coordinate system of position sensing system 407 is referred to above as "position sensor space," this frame of reference/coordinate system may also be referred to as the "patient space." The collected data points in patient space may be used is used to register the patient space to the pre-operative image space of the primary imaging modality (pre-operative images), the intra-operative image space of the secondary imaging modality (intra-operative images), or both.

In some embodiments, instead of, or in addition to, using the dragback method described above for obtaining data points in patient space, individual identifiable locations in the anatomy of the patient are sampled by touching or indicating them with the tracked instrument or endoscope. In some embodiments, a tracked instrument may be temporarily secured in endoscope 403 and not dragged through working channel 423 of endoscope 403. In some embodiments the tracked portion of the tracked instrument is placed near the distal tip 425 of endoscope 403.

In some embodiments, it may be desirable to determine the contortions that endoscope 421 has undergone without the use of images. For example, a colonoscope frequently undergoes loops and other deformations that affect a medical procedure being performed using the colonocsope. Normally, it is difficult to determine these deformations without imaging. If a tracked elongated member is dragged through working channel 423 of endoscope 403, the locus of points gathered as the position of sensor elements in the tracked member are sampled prescribe a shape that is the same as the shape of endoscope 403 within the anatomy of the patient. This information may be used to assist in the medical procedure. In some embodiments, only a single sensor element attached to a slidable elongated member (e.g., a guidewire) is needed to determine this shape. In some embodiments, multiple sensor elements may be fixed or moved along endoscope 403 to determine its path. In some embodiments, motion may be compensated for by using a dynamic reference device such as, for example, a skin motion tracker, an internally-placed catheter, or other dynamic referencing device. Motion may also be compensated for using a gating device such as, for example, an ECG (electroencephalogram), a respiratory gating device, or other gating device.

In an operation 113, the image space path of inserted endoscope 403 is resolved. As before, it is assumed that registration can be performed using an elongated member or other instrument and a distinction need not be made between endoscope 403 and elongated member 421 or other tracked instrument inserted within the anatomy of the patient. In one embodiment, the image space path of endoscope 403 may be "assumed" or "predicted" (i.e. based on centerline path 211 or the "most likely path" 301 calculated using the pre-operative images that were also used to identify the candidate lesions). This assumed image space path of the endoscope may be used, but lacks a direct measure of the endoscope in situ. In other embodiments, the image space path of the endoscope may be based on the actual path of the inserted endoscope observed in the intra-operative images. This "directly measured" path may require a method expressing the coordinates of this path in the same frame of reference as the candidate lesions (e.g., registering the pre-operative images to the intra-operative images).

In an operation 115, the resolved image space path of endoscope 403 and the patient space path of endoscope 403 may be registered. The two paths may be matched using an iterative closest points (ICP), piecewise ICP, or similar algorithm. This enables a registration matrix (or sequence of registration matrices) to be generated. For additional information regarding registration techniques and other information relevant to the invention, see U.S. patent application Ser. No. 11/059,336 (U.S. Patent Publication No. 20050182319), which is hereby incorporated by reference herein in its entirety. In some embodiments, the start and end points of the centerline locus of points may be adjusted so that the centerline points correspond better to the sampled path.

In some embodiments, registration may be accomplished using other techniques as well, including the identification of "fiducials" present in both preoperative images and identified during the examination by for example touching them with a tracked instrument to determine their location in position sensor space. If at least 3 such points are co-located, a registration can be performed using techniques such as the ICP above or simpler methods such as singular valued decomposition. In some embodiments, the fiducials can be naturally occurring landmarks, such as polyps, and in other embodiments, they can be artificial landmarks such as small balls, surgical staples, specially placed needles, or other elements that may be visible in both the pre-operative images and during optical examination with the endoscope. In some embodiments, the dragback method described above may be used together with the landmark based registration or other registration methods.

In some embodiments, the registration takes the form of a rigid transformation matrix. In some embodiments, the registration uses an affine transformation. In some embodiments, several matrices are used at different places. In some embodiments, weighted combinations of matrices are used.

If two representations of the endoscope's path from two different coordinate systems are to resolve the image space path of endoscope 403 (e.g., an assumed path calculated using pre-operative image data and the actual path observed from the intra-operative images), the two representations themselves must first be "matched" or "registered." This registration may utilize 2D-3D or 3D-3D co-registration techniques.

In some embodiments, endoscope 403 or other elongated instrument may be equipped with additional sensor elements that can act as dynamic referencing or tracking sensors, either with multiple sensor elements placed along the length of endoscope 403 or sensor elements located at the most distal end (e.g., distal end 425) of endoscope 403. These will track gross patient movement or movement the filed generator or other portion of position sensing system 207 motion as long as endoscope 403 remains stationary.

In some embodiments, dynamic references (i.e., sensor elements) can be placed into additional catheters, guidewires, or instruments placed elsewhere in/on the patient that are not affected by the exam. The purpose of these sensor elements is to account for patient movement, including that occurring from respiration, or other patient movement.

In some embodiments the dynamic reference may be externally applied in the form of a skin patch or skin reference in which trackable entities have been embedded. Information regarding skin patch devices that can be used as dynamic references or for other purposes in the context of the invention can be found in U.S. patent application Ser. No. 11/271,899 (U.S. Patent Publication No. 20060173269), entitled "Integrated Skin-Mounted Multifunction Device For Use in Image-Guided Surgery," which is hereby incorporated by reference herein in its entirety.

In some embodiments the dynamic reference may be internally applied using needles, catheters, guidewires, or other instruments. In some embodiments, if, for example, skin patch fiducials or internal fiducials are applied to the patient anatomy prior to obtaining the pre-operative images, the fiducials may be used as a "start point" for registration calculations that may ordinarily take an extended amount of time to perform without a reasonable guess of the correct transformation matrix. This is accomplished by the skin patch, fiducials, or other registration objects having features that are visible in the preoperative scan, where the locations of these features are known relative to any sensor elements used for dynamic referencing. Such features can take the form of pathways (i.e. 2D or 3D shapes made from continuous paths or shapes of an imagable material) or as fiducial clusters.

In some embodiments, the skin patch reference (if used) may contain applied directional markings (e.g. printed on the surface of the skin patch reference). These directional markings may point, for example, toward the patient's left, right, head, and/or toe. The positioning of these marks is used as a patient-centric reference system. The patient-centric reference system is used to reorient a display of the patient's anatomy being explored so as to assist the hand-eye coordination of the surgeon such that the tools moved on the display move according to the expectations of the surgeon. In some forms of the display, displayed tools may move in a non-intuitive way unless the display is rotated into the patient-centric coordinate system.

In an operation 117, once registration has been performed, the invention may include a display and navigation step in which endoscope 403 is tracked in an attempt to locate the suspect lesions with the assistance of the position sensor. In one embodiment, this is facilitated by "parking" a tracked instrument (e.g., elongated instrument 421) at the end of endoscope 403's working channel (once any drag-back sampling or other registration sampling that is required has been performed). In one embodiment, endoscope 403 itself may also be tracked using sensor elements attached to or integrated into endoscope 403, as described herein. In one embodiment, an instrument can be inserted into the working channel 423 of endoscope 403, and thus made to assume the shape of working channel 423. This instrument is then made to become rigid in the shape of endoscope 403 (e.g., through tensioning of a cable such as, for example, that used in a "Greenberg Arm," or other methods known in the art) and endoscope 403 is slid, along the instrument, retracing the known path of the rigid path. Alternatively, this type of instrument can be placed into the anatomy prior to the registration and used as a guide for insertion of endoscope 403.

As endoscope 403 and/or tracked instrument 421 (if used as the means to track the endoscope) is moved through the anatomy to inspect its interior, the position of endoscope 403 and/or tracked instrument 421 may be sampled in the reference frame of position sensing system 407. The locations and orientations determined by position sensing system 407 are converted for the display of the patient's anatomy by applying the registration transformation(s). The location of endoscope 403 may then be indicated on the display. In some embodiments, the display may be based on one or both of the pre-operative or intra-operative images of the patient's anatomy. Displays may include, for example, multiplanar reformats, oblique reformatted views, 3D views, 3D perspective views, simplified graphical "cockpit" style views, simplified maps, or other views. Whenever one of the flagged locations (i.e., lesions or other items of interest) is in the proximity of the tracked portion of endoscope 403 or other instrument, the physician may be notified or he or she will be able to determine from the images that he or she is in proximity of the suspect lesion and can look for it.

In an operation 119, one or more of lesions 205a-205f or other items of interest can then be destroyed, biopsied, or otherwise treated, if detected. In one embodiment, tracked elongated instrument 421 (if used in addition to endoscope 403) can be removed from working channel 423 of endoscope 403, and a biopsy, resection, or other treatment or detection device can be introduced into working channel 423 of endoscope 403 (as the suspect will likely be directly visible). Once investigated or treated, the tracked elongated instrument 421 can be reintroduced into working channel 423 of endoscope 403 and again parked at the end of endoscope 403. In some embodiments, there may be enough space for both tracked elongated instrument 421 and the treatment instrument. In some embodiments, the treatment instrument itself may be tracked.

In some embodiments, a tracked treatment instrument may be introduced percutaneously or through an organ wall to perform a biopsy, treatment, resection, or other treatment. In this way, for example, an ablation or biopsy can be performed using a second instrument. The second instrument can be operable either with visual guidance or it can be positioned completely using the electromagnetic guidance described herein. In some embodiments, an imaging device such as a tracked endoscopic ultrasound can be inserted into endoscope 403 to provide additional views. By facilitating percutaneous treatment, candidate lesions on the exterior of an organ being investigated can be accessed, which may not be normally visible internally.

Figure 5B:
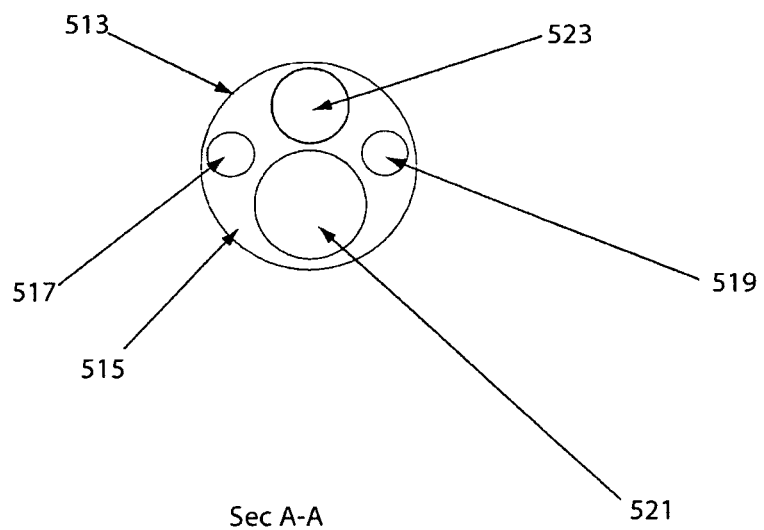

In some embodiments, a device containing trackable sensor elements is not used in conjunction with the endoscope. Instead, the device is used "blind", or for registration only. For example, a steerable catheter might be inserted into colon 201. FIGS. 5A and 5B illustrate an example of a steerable catheter 500 that may be used according to one embodiment of the invention. Steerable catheter 500 may include a deflectable portion 501 with a steerable tip 503. In some embodiments, steerable catheter 500 may include a handle 505 with at least one deflection control knob or other deflection control device 507. The shaft of steerable catheter 500 may include multiple lumens populated by different devices, including a magnetic sensor element 509 with associated lead-wires 511 that exits catheter 500 and is connected to a control unit, in some embodiments.

Section A-A details an embodiment of catheter 500 shown in cross-section. The elongated body of steerable catheter 500 may comprise a tube 513, which may be formed of any relatively soft elastomeric material 515 (e.g., braid reinforced Fluorinated Ethylene Propylene [FEP or Teflon®], polytetrafluoroethylene [PTFE], polyether block amides such as, for example, Pebax® or other material, some of which may be reinforced or include features to render them visible in the imaging modality). Lumens within the tube may include one or more steering wire channels such as channels 517 or 519, a working channel 521, and a channel 523 for a magnetic sensor element (e.g., element 509).

Other "blind" devices may include needles with tip tracking, graspers, steerable forceps, or other elements. When used, the "blind" device is positioned to targets within the anatomy entirely using position sensing system 407 and the display.

In some embodiments, the invention provides for registration-free navigation of an endoscope. In registration-free navigation, sensor elements on a tracked guidewire or other tracked device act simply as a distance measurement device to determine the location of an endoscope relative to a known location. In this embodiment, the relative location of all suspect lesions are calculated relative to each other and landmarks within the anatomy. As each is examined, the location is stored and the distance to the next location of interest is calculated. In this way, the system is self-correcting at each identified location along the path of the endoscope as it is removed. This method may not require registration to be performed prior to use.

Figure 6:
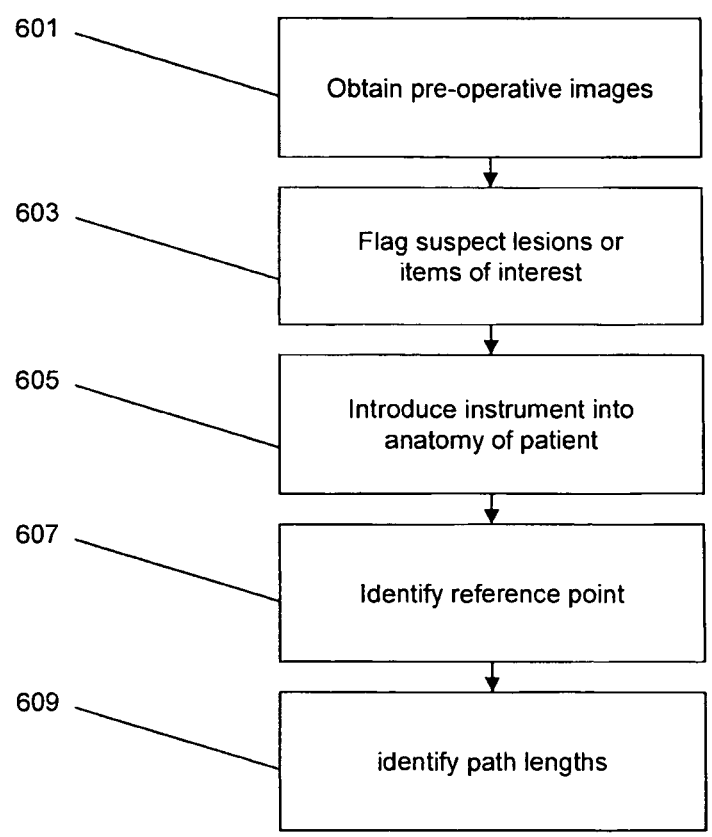
FIG. 6 illustrates an example a process for registration-free navigation during an endoscopic procedure, according to an embodiment of the invention.
Figure 7:
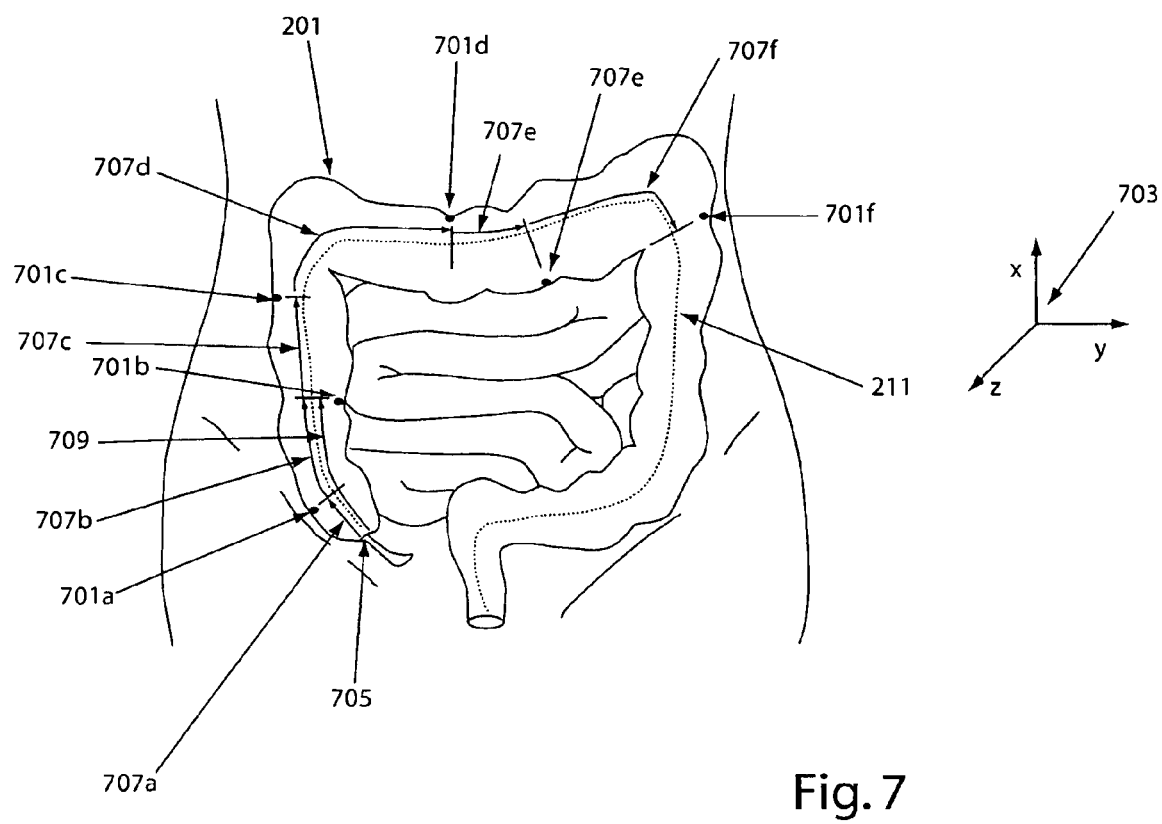
FIG. 7 illustrates an example of an image of a portion of the anatomy of a patient, according to an embodiment of the invention.

FIG. 6 illustrates a process 600, an example of a process for registration-free navigation. In an operation 601, pre-operative images of the anatomy of interest (e.g., colon 201) may be obtained. FIG. 7 an example wherein suspect lesions 701a-701f may be flagged on pre-operative images of colon 201 during a "virtual colonoscopy." This flagging/identification may take place in an operation 603 an may be performed by physician, a computer program, or both. The flagging/identification of operation 603 may include calculating the locations of the flagged suspect lesions 701a-701f in a coordinate system 703, which is a frame of reference intrinsic to the pre-operative images.

In an operation 605, the endoscope is inserted into colon 201. In an operation 607, a reference point 705 within colon 201 is identified (for example, the ileocecal sphincter or appendiceal orifice). In an operation 609, the path length of each of the suspect lesions 701a-701f is identified relative to reference point 705 location along centerline 211 of colon 201. For example, for a lesion 701a, path 707a is the length of the distance along centerline 211 between reference point 705 (e.g., the appeniceal orifice) and suspect lesion 701a. Likewise, path 709 is the length of the distance along centerline 211 between reference point 705 (e.g., the appeniceal orifice) and suspect lesion 701b. Thus by dragging the endoscope back and calculating the distance traversed by the sensor attached to the endoscope, the location of the each next suspect lesion can be determined.

In one embodiment, once the first lesion (i.e., 701a) is encountered, the locations of the next lesions (i.e., 701b-701f) may be calculated relative to it. For example, suspect lesion 701b can be estimated to be located a distance 707b from suspect lesion 701a (or equivalently a distance 709 from reference point 705). In general it may be more accurate to estimate the inter-lesion distances (i.e. 707c, 707d, 707e, 707f), rather than the distance between reference point 705 each successive lesion.

In one embodiment, the physician indicates each lesion 701 as it is encountered and in one embodiment, the lesions 707 and other landmarks are weighted according to their distance from reference point 705. As each lesion is encountered, the expected distance to the next lesions is known from the pre-operative images, since an estimate of that distance is available from the images. Once the first lesion 701a or reference point 705 is located, the endoscope is positioned at the next location (e.g., the next lesion—701b) according to the distance determined from the pre-operative images (distance 707b from lesion 701a or distance 709 from reference point 705). The distance that the endoscope is moved from one lesion to the next is obtained from the sensor elements in the endoscope. By measuring the distance that the endoscope or a tracked instrument in the endoscope moved from a first lesion to a second lesion, the location of the second lesion can therefore be estimated from the pre-operative image estimates without the need for registration.

In one embodiment, these measured distances are augmented using shape information regarding the endoscope or other instrument, as may be determined using a path determination method such as those described herein. This shape information may be helpful in more accurately determining the location of an area of interest. In one embodiment, the suspect lesions can be used to perform a registration. As each lesion is encountered, its position is sampled using a tracked instrument and used to calculate a transformation matrix. In some embodiments, only the nearest candidate lesions to the immediate endoscope location can be used to calculate a local registration, since they are most representative of the local anatomy.

In one embodiment, at least one of the one or more points of interest (e.g., location of lesions, polyps, or other points of interest) within the anatomy of the patient that are identified in image space, may be sampled in patient space and used for registration of patient space coordinates to image space coordinates. The locations of these points of interest may be used bootstrap the registration, thereby enabling the system of the invention to display the location of subsequent points of interest not used in the registration (e.g., obtain position/location of a first few lesions/polyps for registration, after which it becomes "automatic" to locate other lesions/polyps due to the fact that the registration has been performed). As such, the system will automatically display the location of a tracked medical instrument relative to the items of interest whose location has been sampled as well as the items of interest whose location has not been sampled. In one embodiment, the points of interest used to register patient space to image space may be weighted relative to any points of interest whose location is not sampled and used in a registration.

In one embodiment, the invention provides a system for performing and/or assisting in image-guided medical endoscopic medical procedures. FIG. 4 illustrates a system 401, which is an example of a system for performing and/or assisting in image-guided medical endoscopic medical procedures. In one embodiment, system 401 may comprise control unit 411, a control application 427, a tracked medical instrument (e.g., endoscope 403), position sensing system 407, display device 415, and/or other elements.

In one embodiment, control unit 411 may be operatively connected to or include one or more special purpose or general purpose computers 413 and/or other devices having processors cable of responding to and executing instructions in a defined manner. Control unit 411 and/or computer system 413 may include, be associated with, and/or be in operative communication with a memory device that stores any data necessary for the performing the features or functions of the invention such as, for example, image data, position data, orientation data, coordinate data, transformation matrices, and/or other data (e.g., data 417). Control unit 411 and/or computer system 413 may also include, run, and/or support control application 427 comprising one or more software modules for directing and performing one or more data reception, transmission, data processing, and/or other data manipulation operations according to the features and functions of the invention. Other software modules supporting or enabling the various features and functions of the invention may be used.

In some embodiments, the tracked medical instrument may include endoscope 403 that is equipped with at least one working channel, optics for viewing the anatomy present at the distal tip of the endoscope, one or more trackable sensor elements, and/or other elements. The position and/or orientation of the one or more sensor elements may be determined/monitored by position sensing system 407. Position sensing system 407 may be in communication with control unit 411 and/or computer system 413 and may provide sampled position coordinates and orientation information of the one or more sensor elements to control unit 411 and/or computer system 413. An example of position sensing system 407 includes an electromagnetic position sensing system used with electromagnetic sensor elements.

In some embodiments, the tracked medical instrument may include an untracked endoscope or other instrument used in conjunction with a tracked catheter, tracked guidewire, tracked treatment device, and/or other tracked instrument (e.g., elongated instrument 421). In some embodiments, system 401 may not include an endoscope, but may include one or more tracked devices that do not include the optics typically associated with an endoscope.

The system of the invention may also include display device 415 that displays images used in the system and methods of the invention such as, pre-operative images of the anatomy of a patient (including one or more items of interest), intra-operative images of the anatomy of the patient (including an inserted medical instrument and the one or more items of interest), real-time or near-real-time images displaying motion of the tracked instrument relative to the one or more items of interest within the anatomy of the patient, and/or other images or data. In some embodiments, display device 415 may include a computer monitor, a television monitor, a touch screen, a cathode-ray tube, an LCD display device, and/or other display device.

In some embodiments, system 401 may include other elements (e.g., input/output ports, additional devices, additional modules/software). Those having skill in the art will appreciate that the invention described herein may work with various system configurations. Accordingly, more or less of the aforementioned system components may be used and/or combined in various embodiments. Accordingly, more or less of the aforementioned operations of the methods and processes of the invention may be used, and/or may be performed in varying orders. As would also be appreciated, the functionalities described herein may be implemented in various combinations of hardware and/or firmware, in addition to, or instead of, software.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. A method utilizing a computing device in an image-guided medical procedure for indicating on a display controlled by the computing device relative locations of a medical instrument and one or more items of interest within an anatomy of a patient, the method comprising acts of:
   on the computing device:
      receiving one or more preoperative images of the anatomy of the patient that are preoperative to insertion of the medical instrument including the one or more items of interest;
      calculating coordinates of a predicted path in a first preoperative frame of reference corresponding to the one or more preoperative images based on predicted collisions with interior walls of a conduit within the anatomy of the patient in the first preoperative frame of reference;
      determining coordinates of the one or more items of interest within the anatomy of the patient in the first preoperative frame of reference;
      obtaining coordinates of an actual path of the medical instrument within the anatomy of the patient in a second intra-operative frame of reference during the insertion of the medical instrument corresponding to a position sensing system associated with one or more sensor elements within the anatomy of the patient;
      registering the coordinates of the preoperative predicted path of the medical instrument with the coordinates of the actual intra-operative path of the medical instrument based on the predicted collisions with the interior walls of the conduit to produce at least one transformation matrix relating the first preoperative frame of reference to the second intra-operative frame of reference; and
      creating a display indicating relative locations of the medical instrument and the one or more items of interest using the at least one transformation matrix.

2. The method of claim 1, wherein a most-likely path of the medical instrument is predicted based on predicted collisions with the interior walls of the conduit at locations with curvature of greater than ninety degrees.

3. The method of claim 1, wherein the act of determining coordinates of the one or more items of interest utilizes one or more of a computer program and a human operator.

4. The method of claim 1, wherein the one or more items of interest include one or more of a lesion, a polyp, a preoperatively applied fiducial marking, a known tumor, a suspected tumor, a mass, an organ, an osteophyte, a billiary stone, an identifiable hard tissue structures, an identifiable soft tissue structure, an orifice, a junction, a sphincter, a branch point, a tissue transition, a foreign body, and a necrotic zone.

5. The method of claim 1, wherein the medical instrument comprises an endoscope.

6. The method of claim 5, wherein the endoscope further comprises one of a colonoscope, a bronchoscope, a ventricularscope, a cystoscope, a arthroscope, a duodenoscope, a colposcope, a hysteroscope, a laparoscope; a laryngoscope, a sigmoidoscope, or a gastroscope.

7. The method of claim 5, where the endoscope comprises a flexible endoscope.

8. The method of claim 1, wherein the position sensing system comprises one of an electromagnetic position sensing system, a fiber-optic position sensing system, a GPS positioning system, or an optical positioning system.

9. The method of claim 1, wherein the one or more sensor elements comprises one of one or more electromagnetic sensor coils, one or more fiber-optic sensor elements, and one or more optical sensor elements.

10. The method of claim 1, wherein the act of registering the coordinates of the predicted path of the medical instrument with the coordinates of the actual path of the medical instrument utilizes one or more of a drag-back registration, a point to point registration, a combined registration, and a surface registration.

11. The method of claim 1, wherein the act of registering the coordinates of the predicted path of the medical instrument with the coordinates of the actual path of the medical instrument further comprises an act of matching, using a mathematical algorithm, the coordinates of the predicted path of the instrument with the coordinates of the actual path of the medical instrument based on the predicted collisions with the interior walls of the conduit.

12. The method of claim 11, wherein the mathematical algorithm is an iterative closest points (ICP) algorithm.

13. The method of claim 1, wherein the coordinates of the actual path are obtained by sampling the position of the one or more sensor elements located on the instrument while the instrument is moved within the anatomy of the patient.

14. The method of claim 1, further comprising:
   receiving one or more intra-operative images of the anatomy of the patient;
   determining coordinates of a second actual path of the medical instrument within the anatomy of the patient in a third frame of reference corresponding to the one or more intra-operative images; and
   registering the coordinates of the predicted path of the medical instrument with the coordinates of the second actual path of the medical instrument to produce combined coordinates of a path of the medical instrument within the anatomy of the patient,
   wherein registering the coordinates of the predicted path of the medical instrument with the coordinates of the second actual path of the medical instrument further comprises an act of matching, using a mathematical algorithm, the combined coordinates of the second actual path of the medical instrument with the coordinates of the actual path of the medical instrument, and wherein the at least one transformation matrix relates a combined first, second, and third frame of reference.

15. The method of claim 14, wherein registering the coordinates of the predicted path of the medical instrument with the coordinates of the actual path of the medical instrument comprises one of a 2D-3D or 3D-3D registration.

16. The method of claim 1, wherein the display includes one or more of multi-planar reformats, oblique reformatted views, 3D views, 3D perspective views, simplified graphical cockpit-style views, targeting displays, and simplified maps.

17. The method of claim 1, wherein the act of registering the coordinates of the predicted path of the medical instrument with the coordinates of the actual path of the medical instrument further comprises an act of using an externally placed device to begin the registration and to dynamically reference the anatomy of the patient.

18. The method of claim 17, wherein the externally placed device includes marks to indicate placement in a cranial-caudal and anterior-posterior to facilitate manipulation of instruments.

19. A method utilizing a computing device in an image-guided medical procedure for indicating on a display controlled by the computing device relative locations of a medical instrument and a plurality of items of interest within an anatomy of a patient, the method comprising acts of:
on the computing device:
receiving one or more preoperative images of the anatomy of the patient that are preoperative to insertion of the medical instrument including the plurality of items of interest;
determining coordinates of the plurality of items of interest in a first preoperative frame of reference corresponding to the one or more preoperative images;
obtaining coordinates of an actual path of the medical instrument within the anatomy of the patient in a second intra-operative frame of reference corresponding to a position sensing system;
creating a display indicating relative locations of the medical instrument and the plurality of items of interest;
measuring, in the second intra-operative frame of reference, a sensor distance traversed by the medical instrument from a first to a second item of the plurality of items of interest within the anatomy of the patient;
measuring, in the first preoperative frame of reference, an image distance between the first item and the second item based on predicted collisions with interior walls of a conduit between the first item and the second item in the first preoperative frame of reference; and
providing an indication when the sensor distance and the image distance differ by less than a predetermined amount.

20. The method of claim 19, wherein the sensor distance is measured based on predicted collisions at locations with curvature of greater than ninety degrees of the conduit within the anatomy of the patient between the first item and the second item.

21. A system for assisting an image-guided medical procedure relating one or more points of interest within an anatomy of a patient, the system comprising:
a memory device that receives one or more preoperative images of the anatomy of the patient that are preoperative to insertion of a tracked instrument;
the tracked instrument includes one or more sensor elements associated with a position sensing system, wherein the tracked instrument provides coordinates of an actual path of the tracked instrument during the insertion of the tracked instrument within the anatomy of the patient in a second intra-operative frame of reference corresponding to the position sensing system;
a control application configured to
calculate coordinates of a predicted path in a first preoperative frame of reference corresponding to the one or more preoperative images based on predicted collisions with interior walls of a conduit within the anatomy of the patient in the first preoperative frame of reference, and
determine coordinates of the one or more items of interest within the anatomy of the patient in the first preoperative frame of reference corresponding to the one or more preoperative images;
wherein the control application registers the coordinates of the predicted path of the tracked instrument with the coordinates of the actual path of the tracked instrument based on the predicted collisions with the interior walls of the conduit to produce at least one transformation matrix relating the first preoperative frame of reference to the second intra-operative frame of reference; and
a display module that creates a display indicating the relative locations of the instrument and the one or more points of interest using the at least one transformation matrix.

* * * * *